United States Patent [19]
Kauffman

[11] B 3,985,748
[45] Oct. 12, 1976

[54] ISOCYANURATE COMPOUNDS

[75] Inventor: William J. Kauffman, Lititz, Pa.

[73] Assignee: Armstrong Cork Company, Lancaster, Pa.

[22] Filed: Dec. 31, 1974

[21] Appl. No.: 537,711

[44] Published under the second Trial Voluntary Protest Program on January 13, 1976 as document No. B 537,711.

[52] U.S. Cl. ........................ 260/248 NS; 260/75 R
[51] Int. Cl.² ........................................ C07D 251/30
[58] Field of Search .............................. 260/248 NS

[56] References Cited
UNITED STATES PATENTS 3,235,553  2/1966  Sadle ................................ 260/248
3,249,607  5/1966  Taub et al. ......................... 260/248

*Primary Examiner*—John M. Ford

[57] ABSTRACT

Phenylisocyanurate is reacted with ethyl-4-chlorobutyrate in an inert solvent to 25°C. to 150°C. to produce 1,3-bis(3-carbethoxypropyl)-5-phenylisocyanurate. The 1,3-bis(3-carbethoxypropyl)-5-phenylisocyanurate is then heated with a mineral acid to produce 1,3-bis(3-carboxypropyl)-5-phenylisocyanurate.

2 Claims, No Drawings

ISOCYANURATE COMPOUNDS

CROSS-REFERENCE TO RELATED APPLICATIONS

Polyesters derived from 1,3-bis(3-carboxypropyl)-5-phenylisocyanurate are claimed in copending U.S. patent application entitled Linear Polyesters Based on Phenylisocyanurate and Processes for Preparing Same by William J. Kauffman, Ser. No. 537,710, filed 12-31-74.

BACKGROUND OF THE INVENTION

Field of the Invention

This invention relates to novel isocyanurate organic compounds and processes. More particularly, it relates to 1,3-bis(3-carboxypropyl)-5-phenylisocyanurate and intermediates thereof. Additionally, it relates to certain processes related to the preparation of the above compounds.

DESCRIPTION OF THE PRIOR ART

Isocyanurate compositions such as those disclosed in U.S. Pat. No. 3,407,200-Little et al. are useful as intermediates in the preparation of synthetic polymers from which fibers are prepared. These fibers are useful in the manufacture of rope, wearing apparel, and carpeting.

It is, therefore, an object of the present invention to provide the novel isocyanurate compound 1,3-bis(3-carbethoxypropyl)-5-phenylisocyanurate and its hydrolysis product 1,3-bis(carboxypropyl)-5-phenylisocyanurate.

It is a further object of this invention to provide a process whereby a novel compound, 1,3-bis(3-carbethoxypropyl)-5-phenylisocyanurate and its novel hydrolysis product 1,3-bis(3-carboxypropyl)-5-phenylisocyanurate.

SUMMARY OF THE INVENTION

In accordance with the present invention, it has now been discovered that 1,3-bis(3-carboxypropyl)-5-phenylisocyanurate is produced by a process which comprises reacting disodium phenylisocyanurate with ethyl-4-chlorobutyrate in an inert solvent to yield 1,3-bis(3-carbethoxypropyl)-5-phenylisocyanurate as illustrated by the following reaction:

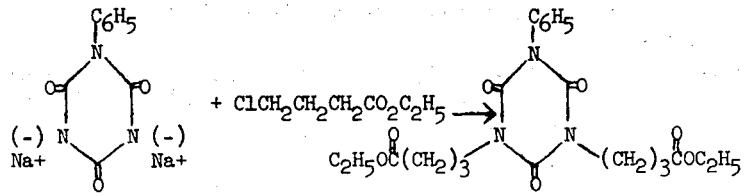

Thereafter, the resultant subject compound is hydrolyzed, by heating the diester compound with aqueous mineral acid, such as hydrochloric acid, or aqueous alkali to the corresponding 1,3-bis(3-carboxypropyl)-5-phenylisocyanurate.

Novel polyesters made by condensing 1,3-bis(3-carboxypropyl)-5-phenylisocyanurate with a polyol such as 1,6-hexanediol exhibit excellent strength and high elasticity rendering them useful in the preparation of fibers.

DESCRIPTION OF THE PREFERRED EMBODIMENT 1,3-bis(3-carboxypropyl)-5-phenylisocyanurate is a solid dibasic carboxylic acid, readily obtainable in crystalline form. It is useful in a number of applications, particularly in the preparation of its polymers such as polyesters. Fibers made from these polyesters exhibit excellent strength and elasticity rendering them useful in the manufacture of wearing apparel and carpeting. It is also useful in forming coatings and molded plastic articles.

1,3-bis(3-carboxypropyl)-5-phenylisocyanurate can be prepared by the alkylation of a reactive cyanuric acid salt, e.g., an alkali metal salt of cyanuric acid with at least two mole equivalents of ethyl-4-chlorobutyrate in an inert reaction medium to form the diester 1,3-bis(3-carbethoxypropyl)-5-phenylisocyanurate. The diester is then hydrolyzed as by exposure to a strong mineral acid, such as concentrated hydrochloric acid to form the diacid.

It has been found preferred to employ disodium phenylisocyanurate in the reaction. However, potassium or other salts can be employed with satisfactory results. Workable concentrations of disodium phenylisocyanurate in the reaction mixture will be about 5 to 50% by weight based on the total weight of the reaction mixture.

Any reaction medium which is inert and which will form a suitable reaction mixture at elevated temperatures can be used. For use in the above reaction, the lower dialkyl-substituted amides of lower carboxylic acids, such as dimethylformamide, diethylformamide, and dimethylacetamide, are suitable solvents. It is preferred to employ dimethylformamide as the inert reaction medium.

The reaction is carried on at an elevated reaction temperature for a time sufficient to bring satisfactory yields. The ethyl-4-chlorobutyrate is added at a reasonable rate to the reaction medium containing disodium phenylisocyanurate maintained at a temperature of about 25°C. to 150°C., about 75°C. usually being suitable. The reaction will be carried on for a time sufficient to ensure an adequate yield, about two to ten hours being ordinarily ample, depending upon the concentration of the reactant employed, the reaction temperature, and the like.

The 1,3-bis(3-carbethoxypropyl)-5-phenylisocyanurate is isolated from the reaction mixture by evaporation under reduced pressure. The crude reaction intermediate compound can be further purified by recrystallization from any suitable solvent such as dimethylformamide, acetonitrile, or carbon tetrachloride.

As mentioned above, the intermediate is convertible to the desired 1,3-bis(3-carboxypropyl)-5-phenylisocyanurate by acid hydrolysis with, for example, a concentrated mineral acid such as concentrated hydrochloric acid. The hydrolysis can be conveniently effected by heating the hydrolysis mixture of the intermediate at an elevated temperature for a sufficient period of time to convert to the desired 1,3-bis(3-carboxypropyl)-5-phenylisocyanurate. An hydrolysis time of about one to ten hours at reflux temperature is usually sufficient to bring about the desired hydrolysis with hydrochloric acid. 1,3-bis(3-carboxypropyl)-5-phenylisocyanurate is recovered and isolated from the hydrolysates by following conventional procedures. Customarily, the 1,3-bis(3-carboxypropyl)-5-phenylisocyanurate is relatively insoluble in most of the mineral acids employed for the hydrolysis, for example, in concentrated hydrochloric acid, and can be recovered from the cooled hydrolysate conveniently by following simple filtration procedures. The 1,3-bis(3-carboxypropyl)-5-phenylisocyanurate compound can be recrystallized as desired, as from methylene chloride.

Usable polyesters can be formed by condensing as by heating at elevated temperatures 1,3-bis(3-carboxypropyl)-5-phenylisocyanurate with required amounts of a diol having at least two carbon atoms, and preferably two to ten carbon atoms. Suitable diols may include, for example, 1,4-butanediol, 1,6-hexanediol, ethylene glycol, diethylene glycol, alpha-propylene glycol and decamethylene glycol. The relative quantities of the 1,3-bis(3-carboxypropyl)-5-phenylisocyanurate and diol can be varied somewhat to alter average polymer chain links, degree of esterification of the carboxyl groups, and the like. To form a largely linear polymer, at least about one mole of diol is employed for each mole of 1,3-bis(3-carboxypropyl)-5-phenylisocyanurate.

Polyesters made by condensing 1,3-bis(3-carboxypropyl)-5-phenylisocyanurate with a polyol as described above exhibit excellent strength and high elasticity rendering them extremely useful in the preparation of fibers for carpets and wearing apparel.

Moreover, 1,3-bis(3-carboxypropyl)-5-phenylisocyanurate and the fibers derived therefrom, are extremely thermally stable and produce low smoke upon combustion.

The following illustrative examples more fully describe the preparation of the 1,3-bis(3-carboxypropyl)-5-phenylisocyanurate.

EXAMPLE 1

Preparation of 1,3-bis(3-carbethoxypropyl)-5-phenylisocyanurate

A quantity of 124 g. (0.5 mole) of disodium phenylisocyanurate is added to 2,000 ml. of dimethylformamide with stirring. Ethyl-4-chlorobutyrate (200 g., 1.3 mole) is added, and the mixture is heated at 75°C. for 8 hours. The dimethylformamide is then removed on a rotary evaporator at reduced pressure leaving a white solid product. The residue is then treated with 1,000 ml. of methylene chloride, washed with water, dried, and concentrated. The viscous product is distilled to yield (90%) 1,3-bis(carbethoxypropyl)-5-phenylisocyanurate (180 g., 0.45 mole).

Preparation of 1,3-bis(3-carboxypropyl)-5-phenylisocyanurate

A mixture of 1,3-bis(3-carbethoxypropyl)-5-phenylisocyanurate (107 g., 0.25 mole) and 900 ml. of concentrated hydrochloric acid is refluxed (100°C.) for 8 hours. Upon cooling to 5°C., a solid precipitates from solution. The solution is concentrated and the residue is recrystallized from methylene chloride to yield (76%) 1,3-bis(3-carboxypropyl)-5-phenylisocyanurate (70 g., 0.19 mole).

EXAMPLE 2

Preparation of 1,3-bis(3-carbethoxypropyl)-5-phenylisocyanurate

In accordance with the procedure of Example 1, a total of 74 g. (0.3 mole) of disodium phenylisocyanurate is added to 800 ml. of dimethylformamide with stirring. Ethyl-4-chlorobutyrate (98 g., .65 mole) is added, and the mixture is heated at 75°C. for 4 hours resulting in a quantitative yield of crude 1,3-bis(3-carbethoxypropyl)-5-phenylisocyanurate which, upon recrystallization from methylene chloride, yields 80% pure 1,3-bis(3-carboxypropyl)-5-phenylisocyanurate (103 g., 0.24 mole).

Preparation of 1,3-bis(3-carboxypropyl)-5-phenylisocyanurate

In like fashion, to Example 1, 50 g. (0.13 mole) of 1,3-bis(3-carbethoxypropyl)-5-phenylisocyanurate is refluxed (100°C.) with 400 ml. of concentrated hydrochloric acid for eight hours. Upon cooling to 5°C., a solid precipitates and is filtered by suction and recrystallized from 800 ml. of water to yield (53%) of 1,3-bis(3-carboxypropyl)-5-phenylisocyanurate (29 g., .07 mole).

What is claimed is:
1. 1,3-bis(3-carbethoxypropyl)-5-phenylisocyanurate.
2. 1,3-bis(3-carboxypropyl)-5-phenylisocyanurate.

* * * * *